(12) United States Patent
Bush, Jr.

(10) Patent No.: US 11,744,619 B2
(45) Date of Patent: Sep. 5, 2023

(54) FACETED BONE PLATE

(71) Applicant: K2M, Inc., Leesburg, VA (US)

(72) Inventor: Charles L. Bush, Jr., Wayne, NJ (US)

(73) Assignee: K2M, Inc., Leesburg, VA (US)

( * ) Notice: Subject to any disclaimer, the term of this patent is extended or adjusted under 35 U.S.C. 154(b) by 245 days.

(21) Appl. No.: 16/376,194

(22) Filed: Apr. 5, 2019

(65) Prior Publication Data

US 2019/0307491 A1 Oct. 10, 2019

Related U.S. Application Data

(60) Provisional application No. 62/653,877, filed on Apr. 6, 2018.

(51) Int. Cl.
*A61B 17/80* (2006.01)
*A61B 17/70* (2006.01)

(52) U.S. Cl.
CPC ...... *A61B 17/7059* (2013.01); *A61B 17/8042* (2013.01)

(58) Field of Classification Search
CPC ..... A61B 17/70; A61B 17/7059; A61B 17/80; A61B 17/8042
See application file for complete search history.

(56) References Cited

U.S. PATENT DOCUMENTS

| | | | |
|---|---|---|---|
| 2,443,363 A * | 6/1948 | Townsend | A61B 17/80 606/71 |
| 4,957,497 A * | 9/1990 | Hoogland | A61B 17/80 606/71 |
| 5,180,381 A | 1/1993 | Aust et al. | |
| 6,152,927 A | 11/2000 | Farris et al. | |
| 6,193,721 B1 | 2/2001 | Michelson | |
| 6,293,949 B1 | 9/2001 | Justis et al. | |
| 6,454,769 B2 | 9/2002 | Wagner et al. | |
| 6,503,250 B2 * | 1/2003 | Paul | A61B 17/7059 606/279 |
| 6,533,786 B1 * | 3/2003 | Needham | A61B 17/1728 606/282 |
| 6,602,256 B1 * | 8/2003 | Hayes | A61B 17/7059 606/296 |
| 6,890,335 B2 | 5/2005 | Grabowski et al. | |
| 7,169,150 B2 | 1/2007 | Shipp et al. | |
| 7,278,997 B1 | 10/2007 | Mueller et al. | |
| 7,303,564 B2 | 12/2007 | Freid et al. | |
| 7,500,976 B2 | 3/2009 | Suh | |
| 7,625,375 B2 | 12/2009 | Garden et al. | |
| 7,651,497 B2 * | 1/2010 | Michelson | A61B 17/8042 606/247 |
| 7,766,947 B2 | 8/2010 | Hawkes et al. | |
| 7,857,839 B2 | 12/2010 | Duong et al. | |
| 7,862,597 B2 * | 1/2011 | Gause | A61F 2/4455 606/290 |
| 8,043,346 B2 | 10/2011 | Markworth | |
| 8,105,366 B2 | 1/2012 | Null et al. | |
| 8,167,919 B2 * | 5/2012 | Foley | A61B 17/8042 606/290 |
| 8,236,034 B2 | 8/2012 | Binder et al. | |
| 8,361,126 B2 | 1/2013 | Perrow et al. | |
| 8,403,969 B2 | 3/2013 | Wallenstein et al. | |

(Continued)

*Primary Examiner* — Christopher J Beccia (74) *Attorney, Agent, or Firm* — Lerner David LLP (57) ABSTRACT

A bone plate that includes an upper surface defined by at least two flat surfaces and a bone contacting surface defined by at least two flat surfaces.

19 Claims, 12 Drawing Sheets

(56) References Cited

U.S. PATENT DOCUMENTS

| | | |
|---|---|---|
| 8,414,651 B2 | 4/2013 | Tyber et al. |
| 8,419,777 B2 | 4/2013 | Walker et al. |
| 8,486,115 B2 | 7/2013 | Fisher et al. |
| 8,500,782 B2 | 8/2013 | Kovach et al. |
| 8,500,811 B2 | 8/2013 | Blain et al. |
| 8,535,354 B2 | 9/2013 | Cummins |
| 8,900,277 B2 | 12/2014 | Perrow et al. |
| 9,078,718 B2 | 7/2015 | Campbell |
| 9,320,549 B2 | 4/2016 | Fraser et al. |
| 9,375,237 B2 | 6/2016 | Keegan et al. |
| 9,381,044 B2 | 7/2016 | Robinson et al. |
| 9,387,087 B2 | 7/2016 | Tyber |
| 9,615,733 B2 | 4/2017 | Nottmeier |
| 9,629,664 B2 | 4/2017 | Altarac et al. |
| 9,655,665 B2 | 5/2017 | Perrow |
| 2004/0122426 A1 | 6/2004 | Michelson |
| 2004/0181226 A1 | 9/2004 | Michelson |
| 2004/0193269 A1 | 9/2004 | Fraser et al. |
| 2004/0204712 A1* | 10/2004 | Kolb ................. A61B 17/7059 606/287 |
| 2004/0210218 A1 | 10/2004 | Dixon et al. |
| 2004/0215195 A1 | 10/2004 | Shipp et al. |
| 2004/0220566 A1 | 11/2004 | Bray |
| 2004/0220571 A1 | 11/2004 | Assaker et al. |
| 2005/0033294 A1 | 2/2005 | Garden et al. |
| 2005/0049593 A1 | 3/2005 | Duong et al. |
| 2005/0049595 A1 | 3/2005 | Suh et al. |
| 2005/0075633 A1 | 4/2005 | Ross |
| 2006/0036250 A1 | 2/2006 | Lange et al. |
| 2006/0122603 A1 | 6/2006 | Kolb |
| 2006/0293668 A1 | 12/2006 | May et al. |
| 2007/0123884 A1 | 5/2007 | Abdou |
| 2007/0173816 A1 | 7/2007 | Metz-Stavenhagen |
| 2009/0287257 A1 | 11/2009 | Hagen |
| 2010/0137916 A1 | 6/2010 | Hynes et al. |
| 2011/0106159 A1 | 5/2011 | Nazeck |
| 2012/0071933 A1 | 3/2012 | DeRidder |
| 2014/0128924 A1 | 5/2014 | Perrow et al. |
| 2014/0200670 A1 | 7/2014 | Chin et al. |
| 2015/0032220 A1 | 1/2015 | Tyber et al. |
| 2015/0230832 A1 | 8/2015 | Fraser et al. |
| 2015/0257804 A1* | 9/2015 | Baynham ............ A61B 17/7059 606/246 |
| 2016/0081818 A1 | 3/2016 | Waugh et al. |
| 2017/0049491 A1 | 2/2017 | Ross et al. |
| 2017/0119537 A1 | 5/2017 | Tepper et al. |
| 2017/0224388 A1 | 8/2017 | Walker et al. |
| 2017/0238974 A1 | 8/2017 | Konieczynski et al. |

* cited by examiner

FACETED BONE PLATE

CROSS-REFERENCE TO RELATED APPLICATIONS

This application claims the benefit of the filing date of U.S. Provisional Application No. 62/653,877, filed Apr. 6, 2018, the disclosure of which is hereby incorporated herein by reference.

BACKGROUND OF THE INVENTION

Bone plates are commonly used to internally fix and stabilize multiple bone fragments, such as in the case of a fracture, or multiple bones that comprise one or more joints, such as vertebrae of a spinal column.

One common bone plate is an anterior cervical plate that is designed to be attached to an anterior side of two or more cervical vertebrae for the purpose of immobilizing, stabilizing, and/or aligning those vertebrae. Cervical plates of the present type are generally elongate so as to span the distance between two or more vertebrae, as required by a particular application. In addition, such plates generally have radial or radiused surfaces that are curved transversely to the spinal axis so as to approximate the spinal curvature of the anterior vertebral bodies to which they are attached. This curvature is referred to as an axial curve as such curve is apparent when viewing the plate axially. Moreover, plates of this type also commonly have radial surfaces curved longitudinally along the spinal axis to restore the natural lordosis of the vertebrae after attachment of the plate. This curvature is referred to as a lordotic curve of a plate. One example cervical plate with such axial and lordotic curves is disclosed in U.S. Pat. No. 7,686,806, the disclosure of which is incorporated by reference herein.

Another common bone plate is a general purpose bone plate that is used for reducing and stabilizing fractures in one of many different bones. Such general purpose bone plates may also have contours that are intended to approximate a bony surface to which the plates are intended to be attached. Since many bones in a mammalian body are curved, many of such bone plates have radial surfaces curved in one or more planes to approximate a curvature of such bones. A general purpose bone plate with such radial surfaces is disclosed in U.S. Pat. No. 8,162,950, the disclosure of which is hereby incorporated by reference herein.

While the foregoing bone plates may be suitable for their intended purpose, the range of combined curves, such as the anatomical curves associated with the axial and lordotic curves mentioned above, significantly varies from patient to patient. Such variations may be compounded by pathology variations that may affect each patient's anatomy in different ways. Thus, the ability to fit an implant to a specific patient can create a challenge from a manufacturing and fit perspective, which may result in significant manufacturing costs and increased intraoperative time.

In addition, the plates discussed above, as with most bone plates, are machined from a blank of raw material into their final form. Contouring a plate, particularly a plate with radial surfaces, can be expensive as radial surfaces with particularly specified radii of curvature can require significant machine time to achieve the required contour. Additionally, these processes often result in a significant amount of wasted material, especially when the exacting dimensions for a particular plate are not met. In a world where healthcare costs are increasing at a rapid rate, further improvements are desired—particularly those that reduce manufacturing costs of orthopedic implants, such as bone plates.

BRIEF SUMMARY OF THE INVENTION

In a first aspect of the present disclosure, a bone plate includes an upper surface defined by at least two flat surfaces, and a bone contacting surface defined by at least two flat surfaces.

Additionally, the upper surface may include three flat surfaces, and the bone contacting surface may include three flat surfaces. Alternatively, the upper surface may include five flat surfaces, and the bone contacting surface may include five flat surfaces. Also, the flat surfaces may extend in a direction of the width of the plate. The flat surfaces may also extend in a direction of the length of the plate.

Continuing with this aspect, the bone plate may include at least one bone screw hole and at least one blocker hole. A countersink may at least partially surrounding the blocker hole. Such countersink may be defined by a channel extending along a length of the plate. The bone plate may also include two bone screw holes, a blocker hole disposed between the two bone screw holes and a blocker disposed in the blocker hole. The blocker may be movable between a first position in which bone screws can be placed in the bone screw holes and a second position in which the bone screws may be prevented from removal from the bone screw holes. The bone plate may be an anterior cervical plate. The bone plate may be designed to fuse two levels.

In another aspect of the present disclosure, a bone plate includes an upper surface, a bone contacting surface, at least one bone screw hole, and at least one blocker hole at least partially surrounded by a countersink. The countersink is defined by a channel extending along a length of the plate.

Additionally, the upper surface may include three flat surfaces, and the bone contacting surface may include three flat surfaces. Alternatively, the upper surface may include five flat surfaces, and the bone contacting surface may include five flat surfaces. The flat surfaces may extend in a direction of the width of the plate. The flat surfaces may also extend in a direction of the length of the plate.

Furthermore, the bone plate may also include two bone screw holes, a blocker hole disposed between the two bone screw holes and a blocker disposed in the blocker hole. The blocker may be movable between a first position in which bone screws can be placed in the bone screw holes and a second position in which the bone screws may be prevented from removal from the bone screw holes. The bone plate may be an anterior cervical plate, or another type of bone plate for a non-vertebral bone(s), such as a long bone, in a mammalian body.

BRIEF DESCRIPTION OF THE DRAWINGS

The features, aspects, and advantages of the present invention will become better understood with regard to the following description, appended claims, and accompanying drawings in which:

DETAILED DESCRIPTION

As used herein, when referring to the disclosed bone plates and associated instruments, the term "proximal" means closer to the operator or in a direction toward the operator, the term "distal" means more distant from the operator or in a direction away from the operator, the term "medial-to-lateral" means from one side of the body of the patient to the other, the term "cephalad" means toward the head of the patient, and the term "caudal" means away from the head of the patient. Also, as used herein, the terms "about," "generally," and "substantially" are intended to mean that slight deviations from absolute are included within the scope of the term so modified.

FIGS. 1A through 1I depict a first embodiment bone plate 100 according to the present invention. As best shown in the top views of FIGS. 1A and 1D, bone plate 100 includes an upper surface 110, a plurality of screw holes 111 for receiving bone screws, a plurality of blocker holes 113 for receiving blockers and a plurality of graft windows 115. Upper surface 110 is, in turn, defined by three flats 112, 114 and 116, with screw holes 111 substantially located on flats 112 and 116 and blocker holes 113 located on flat 114. A countersink surrounds each blocker hole 113 and allows for an associated blocker, such as the blocker 150 depicted in FIG. 1I, to be substantially flush with the remainder of the surrounding portions of flat 114. Blocker 150 is depicted as a washer 152 and retaining screw 154 combination. However, other blockers are contemplated, such as the rotatable blocker 450 shown in FIGS. 4C-4E and described further below. Each screw hole 111 is shown configured in a manner that allows bone screws 160 to be placed therethrough at varying angles, and such that the head of those screws 160, when placed, are substantially flush or below upper surface 110.

Figure 1A:
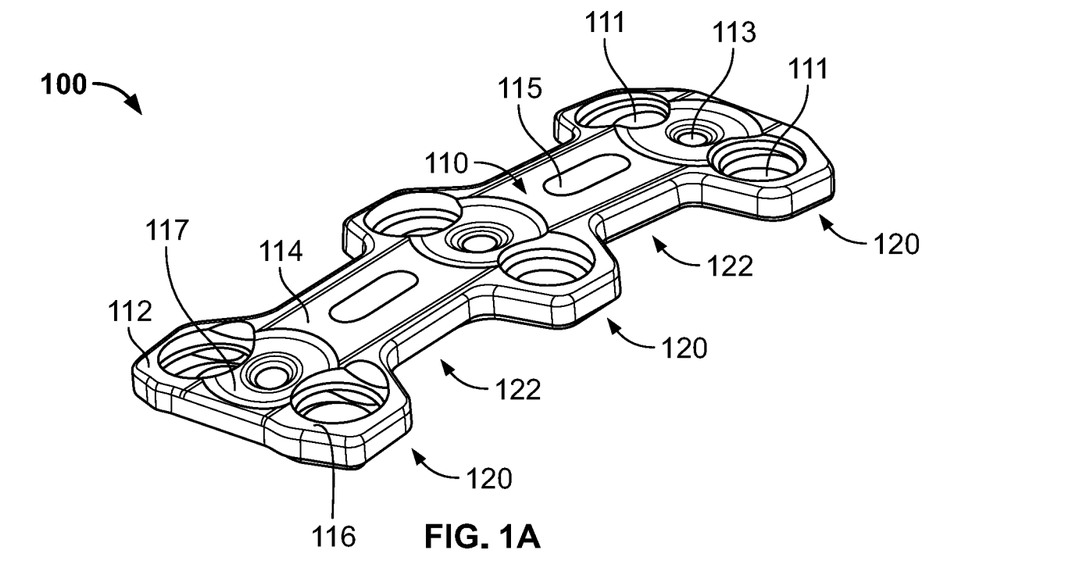
FIG. 1A is a top perspective view of a bone plate according to one embodiment of the present invention.
Figure 1B:
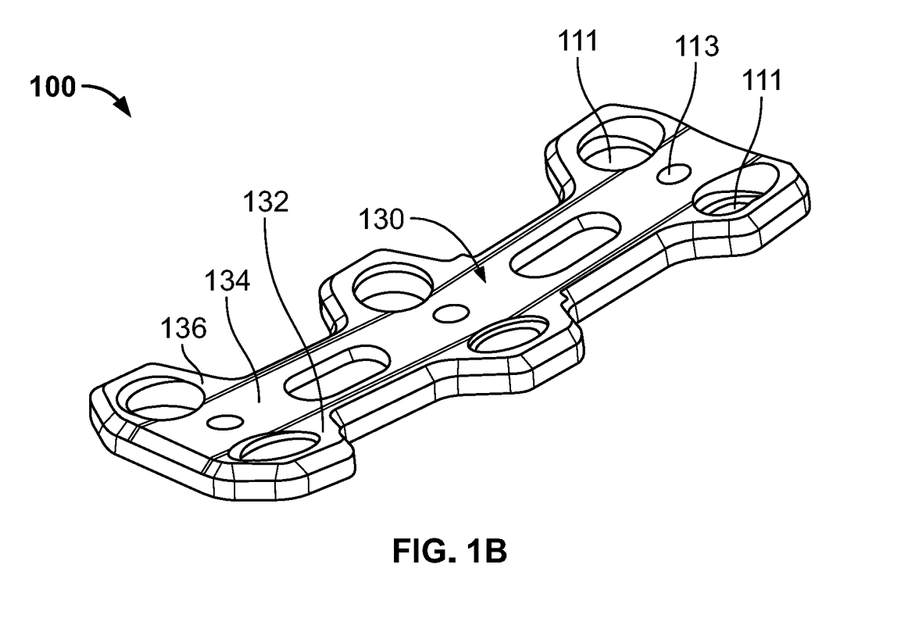
FIG. 1B is a bottom perspective view of the bone plate of FIG. 1A.
Figure 1C:
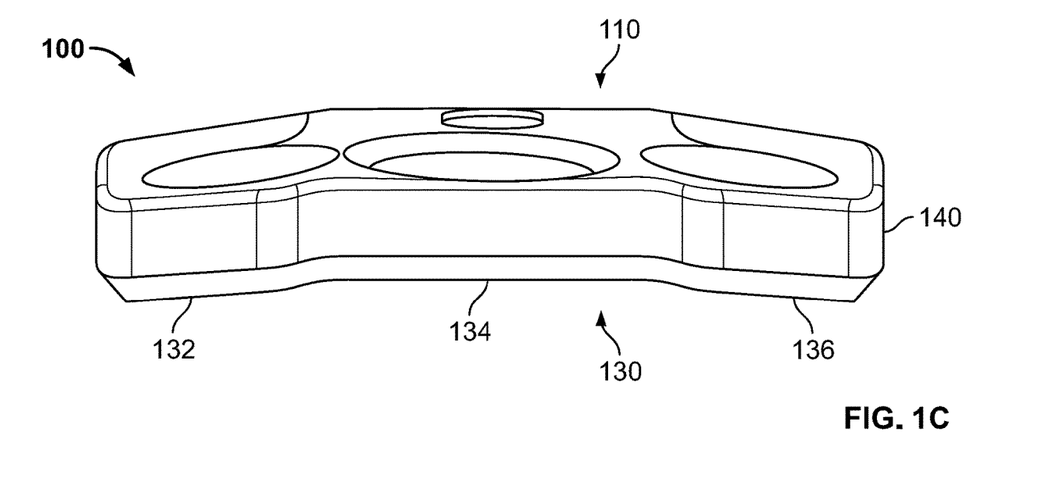
FIG. 1C is a side view of the bone plate of FIG. 1A.
Figure 1D:
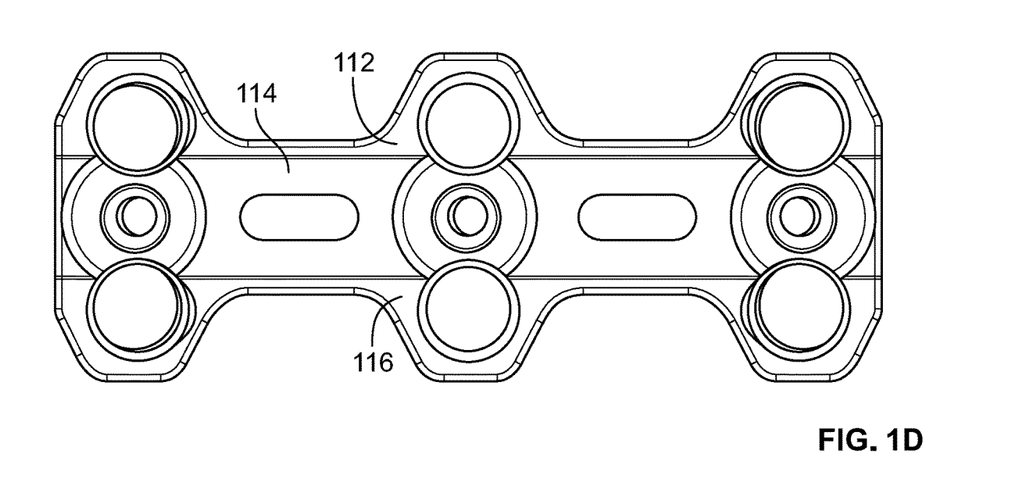
FIG. 1D is a top view of the bone plate of FIG. 1A.
Figure 1E:
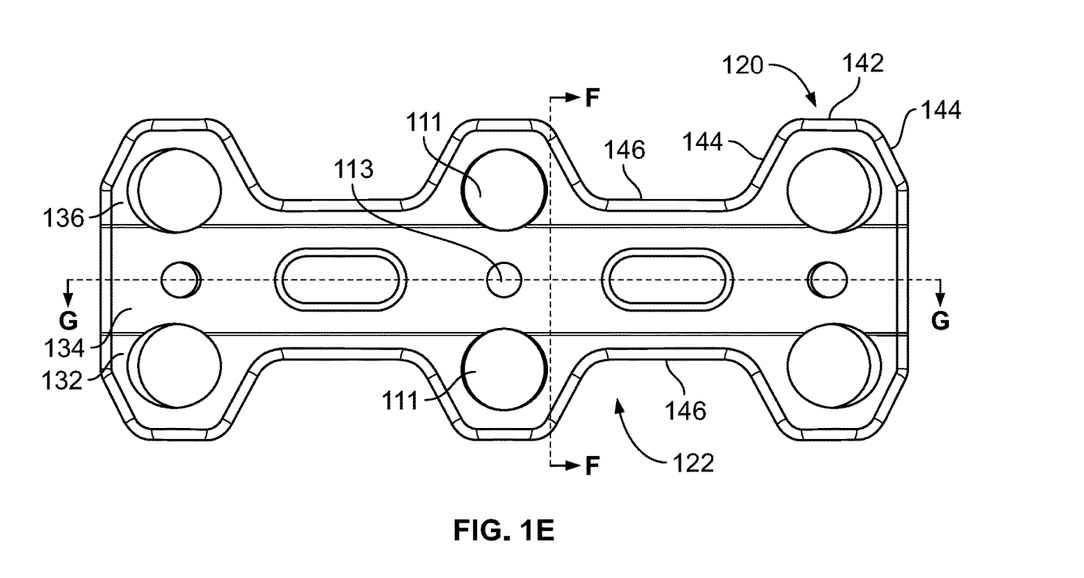
FIG. 1E is a bottom view of the bone plate of FIG. 1A.
Figure 1F:
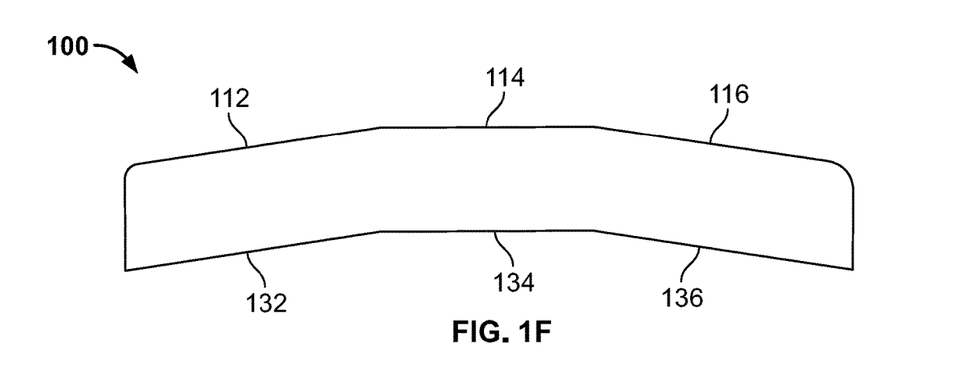
FIG. 1F is a schematic cross-sectional representation depicting the medial-to-lateral configuration of the bone plate of FIG. 1A taken along line F-F of FIG. 1E.

As best shown in the bottom views of FIGS. 1B and 1E, bone plate 100 also includes bone contacting surface 130, which is defined by three flats 132, 134 and 136. Those figures also depict that screw holes 111, blocker holes 113 and graft windows 115 extend entirely through the plate from upper surface 110 to bone contacting surface 130. The aforementioned flats 112, 114, 116, 132, 134 and 136, as best shown in FIGS. 1C and 1F, are provided in lieu of the typical curvatures of bone plates that extend in medial-to-lateral directions. Of course, as will be discussed more fully below, similar flats may extend in other directions, such as in the cephalad-to-caudal direction.

As illustrated in FIGS. 1A, 1B, 1D and 1E, the overall shape of bone plate 100 is defined by three wider sections 120 and two narrower sections 122. The particular configuration shown allows bone plate 100 to be utilized in fusing two levels of a spine. In other words, plate 100 is designed to be placed against and fixed to three separate vertebrae. Two bone screws are to be placed through screw holes 111 on each wider section 120 and into one of the three vertebrae. These screws are in turn prevented from inadvertent removal (e.g., backout) by blockers disposed in blocker holes 113. The plate is further configured so that when attached, graft windows align with the disc spaces between such vertebrae. Thus, wider sections 120 are largely disposed over the vertebral bodies themselves, while narrower sections 122 are largely disposed over the non-bone, disc portions.

Although shown as a two level plate, it is noted that other embodiment plates according to the present invention can be designed for the fusion of any number of levels of the spine of a patient—simply by modifying the amount of wider and narrower sections included. For instance, a single level plate would include two wider sections 120 and one narrower section 122, while a three level plate would include four wider sections 120 and three narrower sections 122. Moreover, differently shaped plates are contemplated in accordance with the present invention. For instance, as opposed to the polygonal-like shapes of sections 120 and 122, more rounded (e.g., convex and concave) sections can be provided. Indeed, below discussed bone plate 200 is such a variation according to the present invention.

As noted above, the particular screw holes 111, blocker holes 113 and countersinks 117 are designed such that the screws placed through holes 111 and blockers disposed in holes 113 are as flush as possible with upper surface 110. However, other embodiments are contemplated in which differently configured holes are contemplated that may or may not result in such flush placement. Screw holes 111 are shown as allowing placement of screws at multiple angles, but other embodiments may only allow placement of screws at a single angle. For instance, it is contemplated to incorporate threaded locking screw holes, combination locking and non-locking screw holes and solely non-locking screw holes, to name a few. Examples of these types of holes are disclosed in U.S. Pat. Nos. 6,602,255; 7,686,806; 8,556,944; 8,388,663; 8,906,077; 9,351,775; and 8,668,723, the disclosures of which are hereby incorporated by reference herein, although any type of screw hole known in the art is possible.

Likewise, although blocker hole 113 is shown disposed between two screw holes 111 such that an associated blocker will prevent inadvertent removal of screws placed through each screw hole 111, other blocker designs can be employed. By way of example, many different types of blocker designs are known in the prior art and can be utilized in the bone plates according to the present invention, including individual blockers that would only prevent inadvertent removal from a single screw hole and blockers that are associated with more than just two holes. Some examples are disclosed in the aforementioned and incorporated patents, as well as others existing in the prior art. Finally, particularly shaped graft windows 15 are shown in the figures, but such elements may be of many different shapes.

With particular attention to the cross-sectional representation of FIG. 1F, upper surface 110 is shown as convex in nature and bone contacting surface 130 is shown as concave in nature. However, rather than consisting of single curves, like in traditional bone plate designs, those surfaces are made up of flats 112, 114 and 116 and flats 132, 134 and 136, respectively. In other words, the traditional medial-to-lateral curvatures of the upper and lower surfaces of bone plates like plate 100 are replaced with flat surfaces that exhibit no radial surfaces yet approximate a radius. These surfaces provide several benefits. Flat surfaces are quicker and cheaper to manufacture than curved surfaces. Indeed, as noted above, the preferred method of manufacturing bone plates such as plate 100 is to machine them from a single blank of material. Machining flat surfaces is much easier than machining curved surfaces, and it has been found that the inclusion of flat surfaces approximates the traditional curves enough to maintain the applicability of the plates to the bone.

Figure 5A:
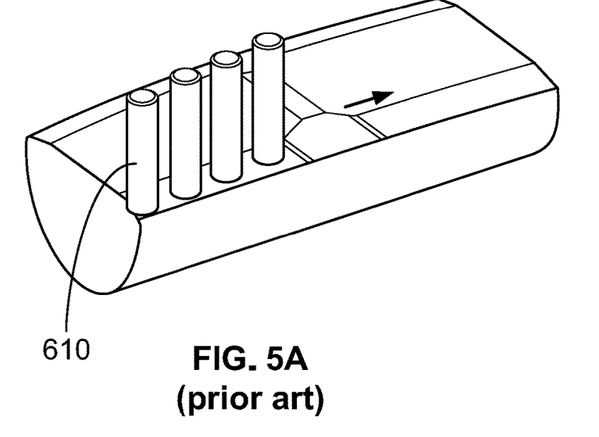
FIGS. 5A and 5B depict one method of forming a radial curve on a bone plate according to an embodiment of the present disclosure.
Figure 5B:
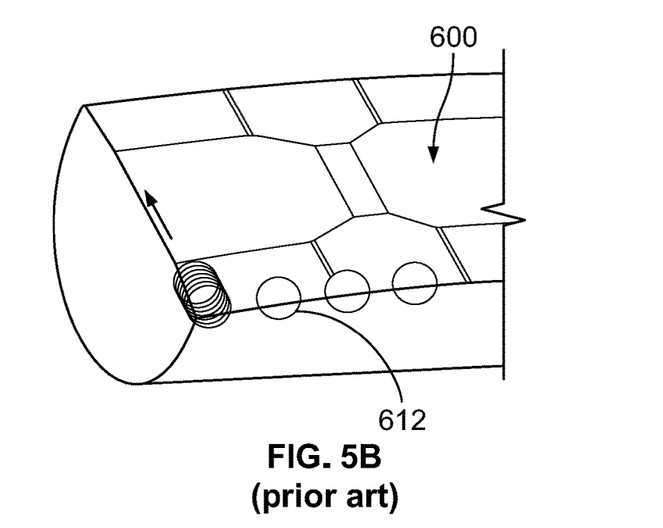

To further illustrate the manufacturing benefits of flat surfaces as compared to radial surfaces, FIGS. 5A and 5B depict a sweep milling approach that is typically used to form radial surfaces commonly found in existing bone plates. In the sweep milling approach, a widthwise oriented mill-bit 610 sweeps along a surface of a blank of material 600. The footprint 612 diameter/width of mill-bit 610 relative to the surface to be formed is very small, typically about 0.1 mm, so as to ensure a smooth, uniform radial surface. Thus, numerous milling paths, which may be oriented in multiple different directions, are required to cover the desired surface area. Moreover, the entire operation is typically repeated at least twice in order to achieve the desired surface finish.

Figure 6:
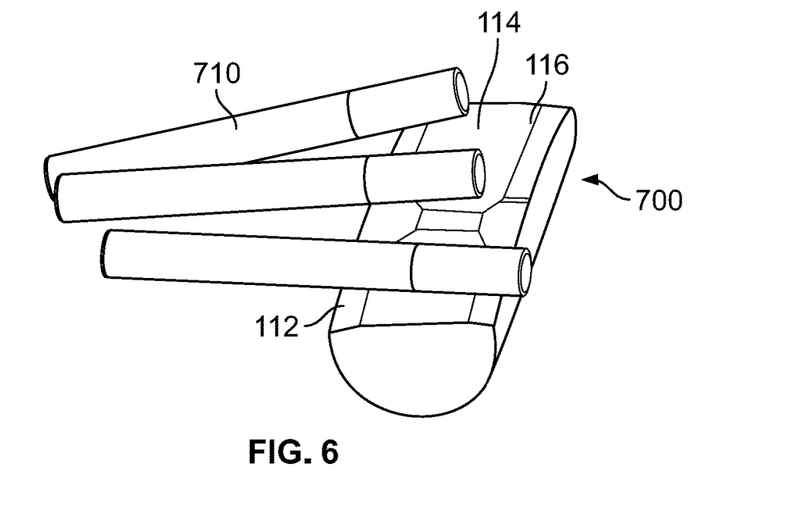
FIG. 6 depicts a method of forming faceted surfaces of the bone plates of FIGS. 1A and 2A according to an embodiment of the present disclosure.

In contrast, as shown in FIG. 6, plate 100 may be formed using a roll milling approach in which a mill-bit 710 is oriented lengthwise relative to the workpiece 700 so that a larger cutting area is exposed to the block of raw material 700 relative to that of the sweep milling approach described above. In this regard, the length of the cutting footprint of mill-bit 710 is substantially equal to the width of the flat or faceted surface formed by such bit 710. Thus, only one milling path is needed for each flat. For example, FIG. 6 depicts flats 112, 114, and 116 of plate 100 being formed from workpiece 700 via corresponding first, second, and third paths by mill-bit 710. Similarly, flats 132, 134, and 136 of lower surface of plate 100 may be formed by another three passes of mill-bit 710 or another mill-bit. This plate construction approach has been found to achieve a cycle time reduction of about 70% and an increased lifecycle of the milling tools. However, it should be understood that other milling approaches can be taken, such as the sweep milling approach with a large diameter mill-bit Another benefit of the flats, particularly those that contact bone, such as flats 112, 114, and 116, is that such surfaces provide a best-fit configuration for the axial curves of the patient's anatomy. Stability provided on what is typically uneven and non-symmetrical axial and lordotic curves of a patient's anatomy directly impacts the operator's ability to place, position, and maintain the desired location of the bone plate on the bone. However, due to variations in a patient's anatomy, radial bone plates are often unstable as the contact point(s) between the bone and the plate may be focused in one region of the plate, such as at the plate's centerline, which can induce "rocking" of the plate. Such instability can directly impact bone screw positioning and purchase into bone. Moreover, sensitive anatomy, such as arteries, nerves, and the like may be placed at risk where the plate can slide or move while the operator is attempting to position screws. Bone plates are often manipulated, such as by bending, during the surgical procedure to help match the implant to the patient. However, this can take significant time and may not provide an optimal result. The flats described herein, such as flats 112, 114, and 116, help provide stability as such flats form a best-fit configuration that provides multiple points of contact or tangents that helps stabilize the implant against the bone. This helps eliminate or reduce rocking of the bone plate which is often experienced with radial surfaces, as mentioned above. Moreover, the best-fit configuration helps reduce the potential need for contouring the bone plate to be specific to the patient's anatomy, thereby possibly reducing intraoperative time. The stability provided by flats 112, 114, and 116 at the bone contacting side of plate 100 provides a more stable platform which can also make placement of screws through holes 111 easier and more accurate.

Figure 1G:
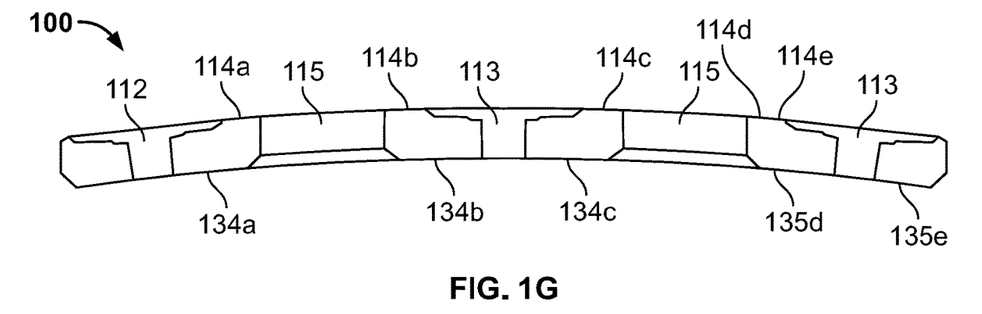
FIG. 1G is a schematic cross-sectional representation depicting a cranial-to-caudal configuration of the bone plate of FIG. 1A taken along line G-G of FIG. 1E.
Figure 1H:
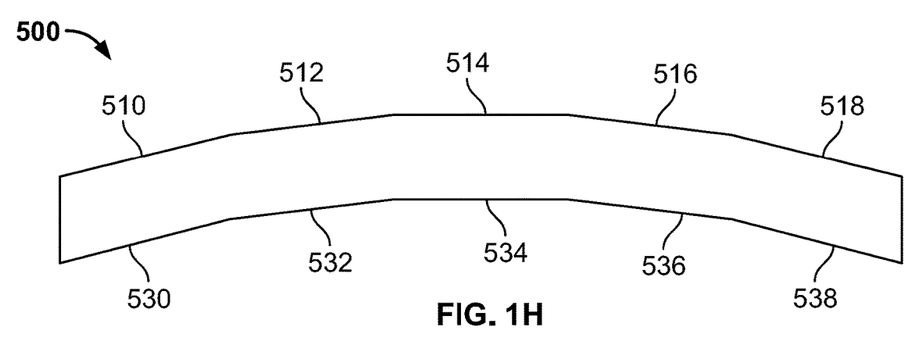
FIG. 1H is a schematic cross-sectional representation depicting the medial-to-lateral configuration of a bone plate according to another embodiment of the present disclosure.
Figure 1I:
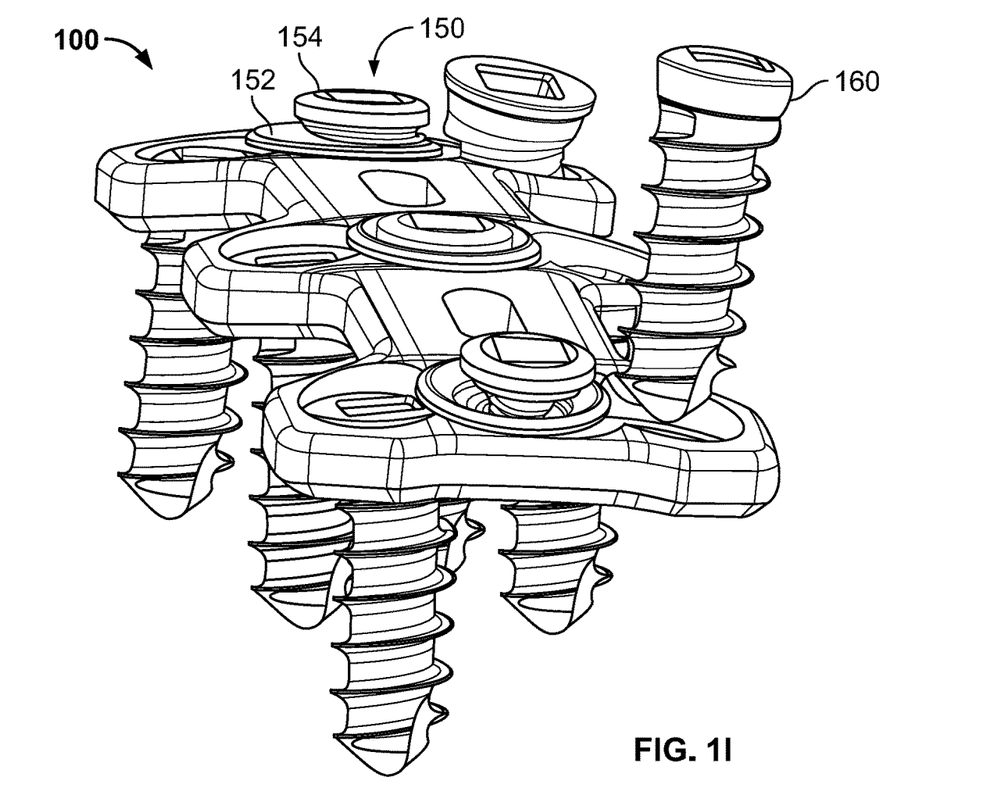
FIG. 1I is a perspective view of the bone plate of FIG. 1A in conjunction with bone screws and a screw blocker embodiment.
Figure 2A:
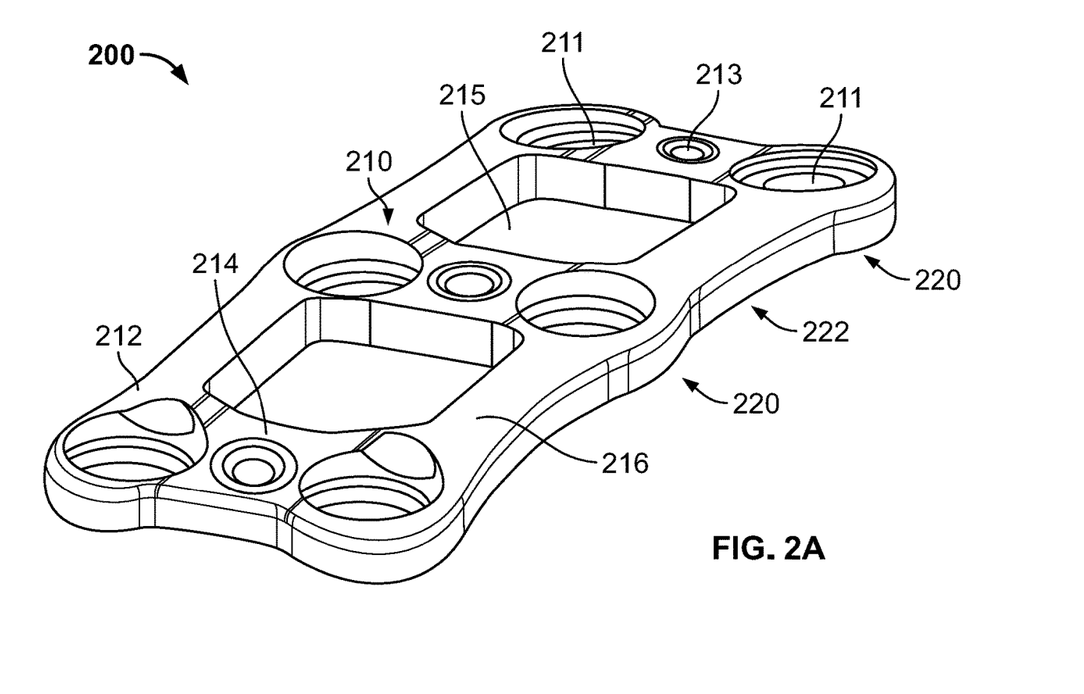
FIG. 2A is a top perspective view of a bone plate according to another embodiment of the present disclosure.
Figure 2B:
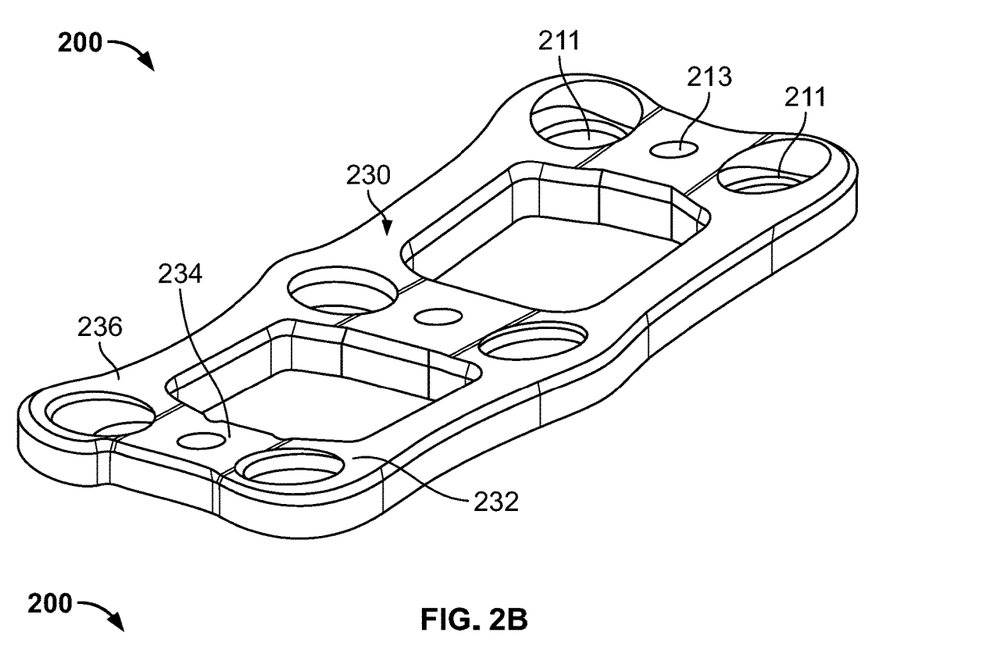
FIG. 2B is a bottom perspective view of the bone plate of FIG. 2A.
Figure 2C:
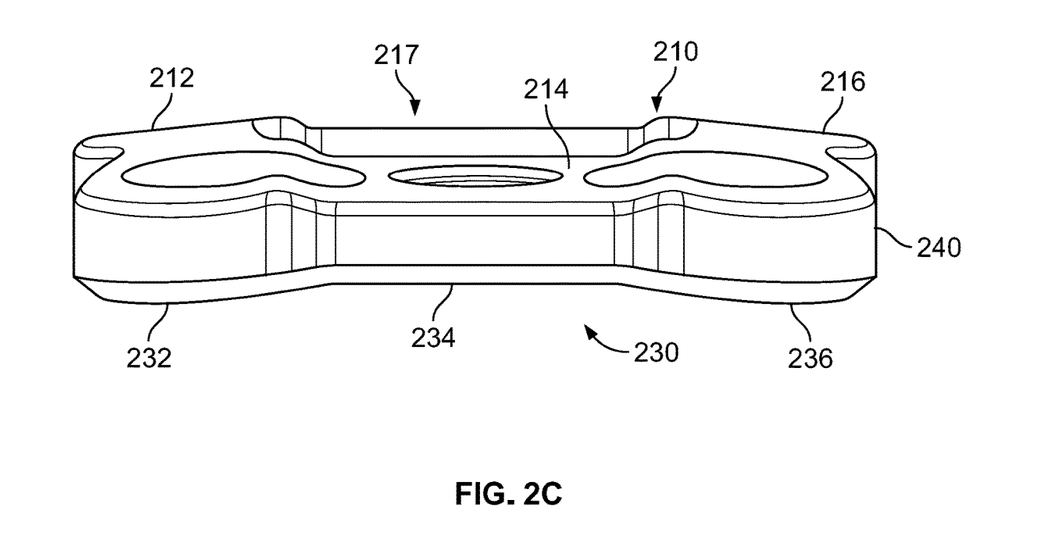
FIG. 2C is a side view of the bone plate of FIG. 2A.
Figure 2D:
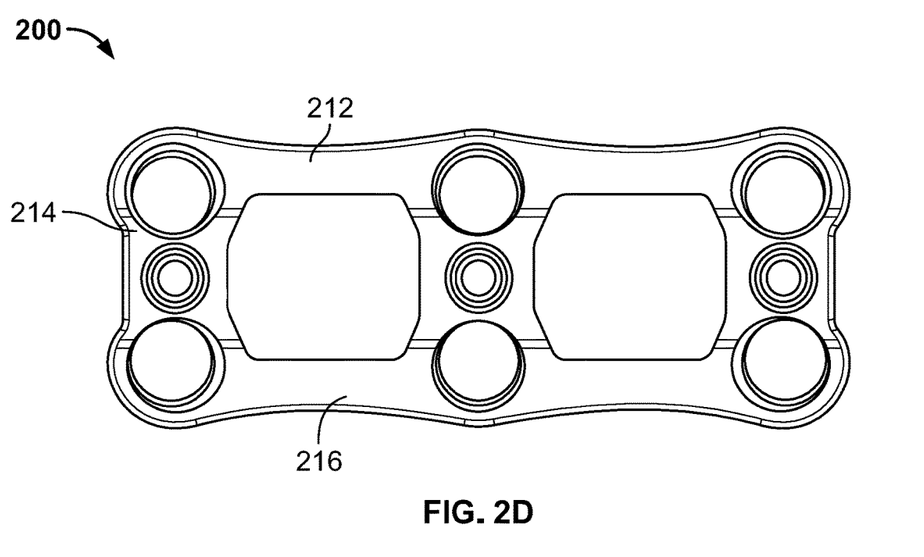
FIG. 2D is a top view of the bone plate of FIG. 2A.
Figure 2E:
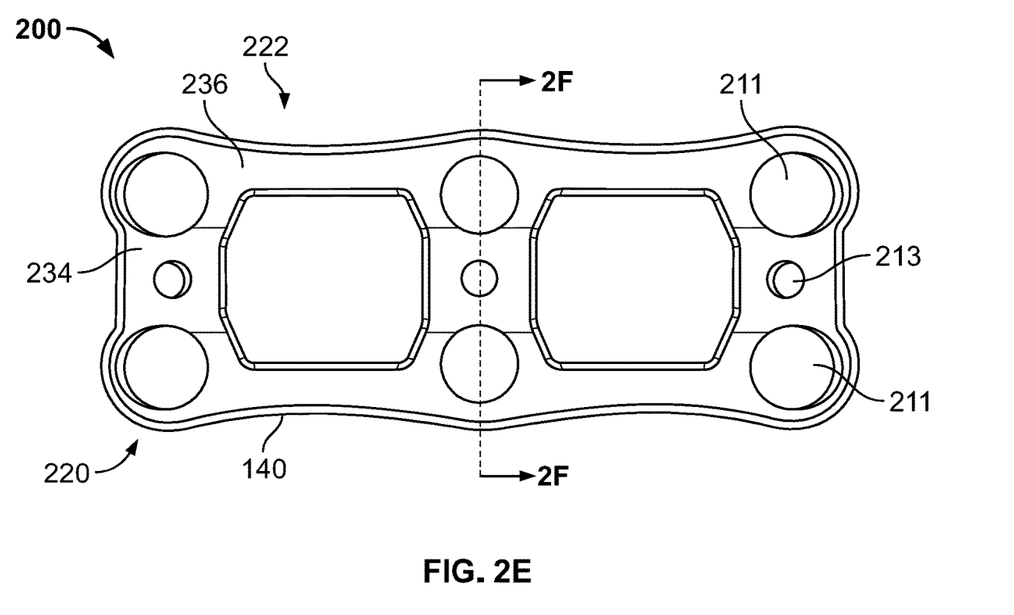
FIG. 2E is a bottom view of the bone plate of FIG. 2A.
Figure 2F:
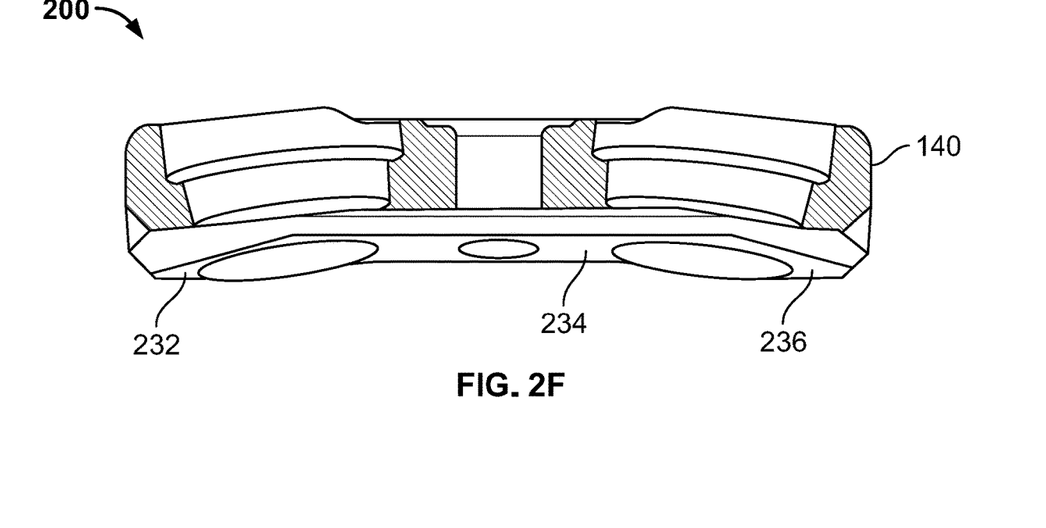
FIG. 2F is a cross-sectional view taken along line F-F of FIG. 2E.

In addition, it is contemplated that the upper and bone contacting surfaces 110, 130 can include more than just the three flat surfaces shown in the embodiment of FIGS. 1A-F. For instance, FIG. 1H depicts an embodiment 500 in which an upper surface consists of five flats 510, 512, 514, 516, 518, and a bone contacting surface consists of five flats 530, 532, 534, 536, 538. The inclusion of more, and shorter, flat surfaces allows the plate to more closely approximate the traditional curves of bone plates of this type, while at the same time maintaining the aforementioned benefits of the present invention.

In addition to the medial-to-lateral configurations noted above, it is noted that bone plates according to the present invention can also exhibit similar configurations in the cephalad-to-caudal direction. For instance, bone plate 100 may be curved or radiused in this direction in order to allow for the restoration of the natural lordosis of the vertebrae, (i.e. the natural curvature of the spine). More specifically, flats 112, 114, 116, 132, 134, and 136 are each flat in a medial-to-lateral plane, but may each be radiused in a cranial-to-caudal plane. However, according to the present invention, those curves can be replaced with flats similar to those discussed above. For example, as shown in FIG. 1G, flats 114 and 134, which are flat in the medial-to-lateral direction, may be segmented into multiple flats 14a-e and 134a-e, respectively, in the cranial-to-caudal direction. However, as depicted, the angles formed between the intersections of adjacent flats 114a-e and 134a-e in the cranial-to-caudal direction are larger relative to that between flats 112, 114, 116 and 132, 134, 136 in the lateral-medial direction so as to be almost undiscernible from a curve. This is due to the greater length of plate 100 in the cranial-to-caudal direction, the greater number of flats, and because the flats 114*a-e* and 134*a-e* approximate a larger radius of curvature than that of flats 112, 114, 116, 132, 134, and 136. Again, the more flats included, the closer the approximation of the curve will be, and the inclusion of flats in this cephalad-to-caudal direction will enjoy similar benefits to the above-discussed medial-to-lateral flats.

Also in line with the reduction in cost and difficulty associated with manufacture, it is contemplated that other embodiment plates according to the present invention may include a single channel extending along its upper surface and the longitudinal axis of the plate. This channel would be included in lieu of providing countersinks 117 around each blocker hole 113, as the channel would effectively provide the necessary countersink for the blockers, without the need for creating individual more-complicated countersinks. Like with the inclusion of the aforementioned flats, a single channel countersink improves the ease of manufacture of such a plate, as described further below.

FIGS. 2A-2F depict another embodiment bone plate 200. For ease of review, like elements are accorded like reference numerals to that of bone plate 100, but within the 200-series of numbers. For instance, bone plate 200 includes upper surface 210 defined by flats 212, 214 and 216, and bone contacting surface 230 defined by flats 232, 234 and 236. However, bone plate 200 also differs from bone plate 100 in a number of ways. First, rather than including the relatively polygonal and significantly differently sized wider and narrower sections 120 and 122, bone plate 200 includes convex wider sections 220 and concave narrower sections 222. Because these sections are much closer in size, bone plate 200 appears more rectangular in shape. The size and shape of plate 200 may make it more suitable for use on larger vertebrae or even in different areas of the spine. In addition, the overall increase in size of at least sections 222 allows for the inclusion of larger graft windows 215.

Figure 3A:
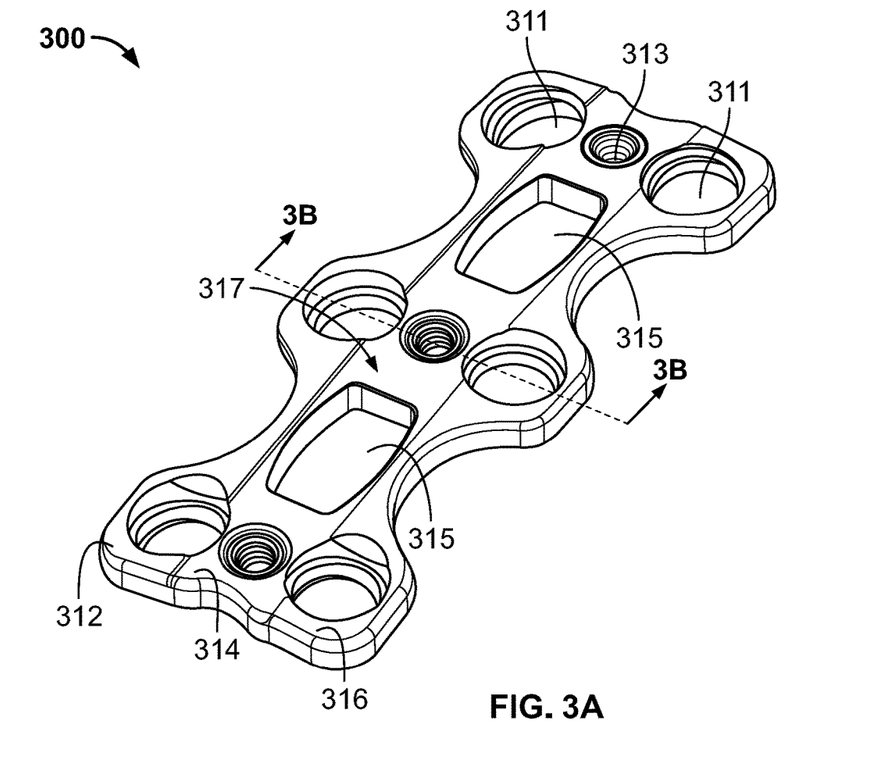
FIG. 3A is a top perspective view of a bone plate according to a further embodiment of the present disclosure.
Figure 3B:
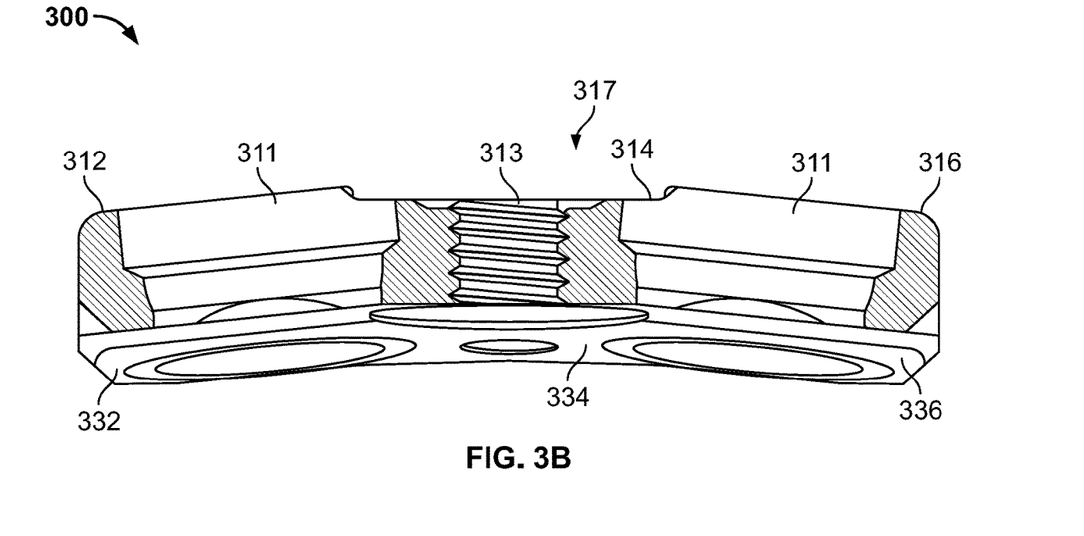
FIG. 3B is a cross-sectional view of the bone plate of FIG. 3A taken along line B-B.

FIGS. 3A and 3B depict a further embodiment bone plate 300. For ease of review, like elements are accorded like reference numerals to that of bone plate 100, but within the 300-series of numbers. For instance, bone plate 300 includes an upper surface defined by flats 312, 314 and 316, and a bone contacting surface defined by flats 332, 334 and 336, as best shown in FIG. 3B. However, bone plate 300 also differs from bone plate 100 in a number of ways. First, graft windows 315 are larger than that in bone plate 100 and are also rectangular with curved side portions that form concavities in bone plate 300.

Secondly, bone plate includes a single channel 317 that is cut along the upper surface in lieu of countersinks, such as countersinks 117, which surround each blocker hole 113. In this regard, channel 317 longitudinally extends between flats 312 and 316, thereby depressing flat 314 to a lower elevation than that of flat 114. Channel 317 provides a similar benefit to countersinks 117 in that it allows for a screw blocker, such as blocker 150, engaged to blocker hole 313 to have a low profile. However, channel 317 provides an additional benefit over that of countersinks 117 in that machining such single channel 317 into plate 300 is generally faster than machining each of countersinks 117, thereby further improving the benefits realized by the flats, as described above.

Figure 4A:
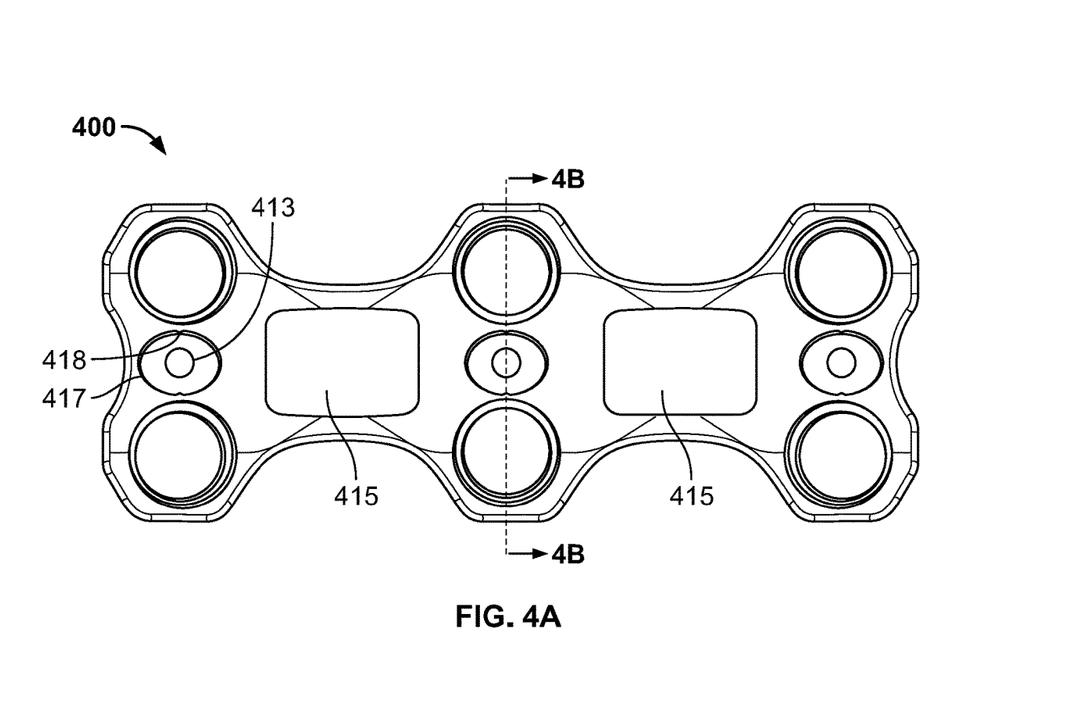
FIG. 4A is a top view of a bone plate according to an even further embodiment of the present disclosure.
Figure 4B:
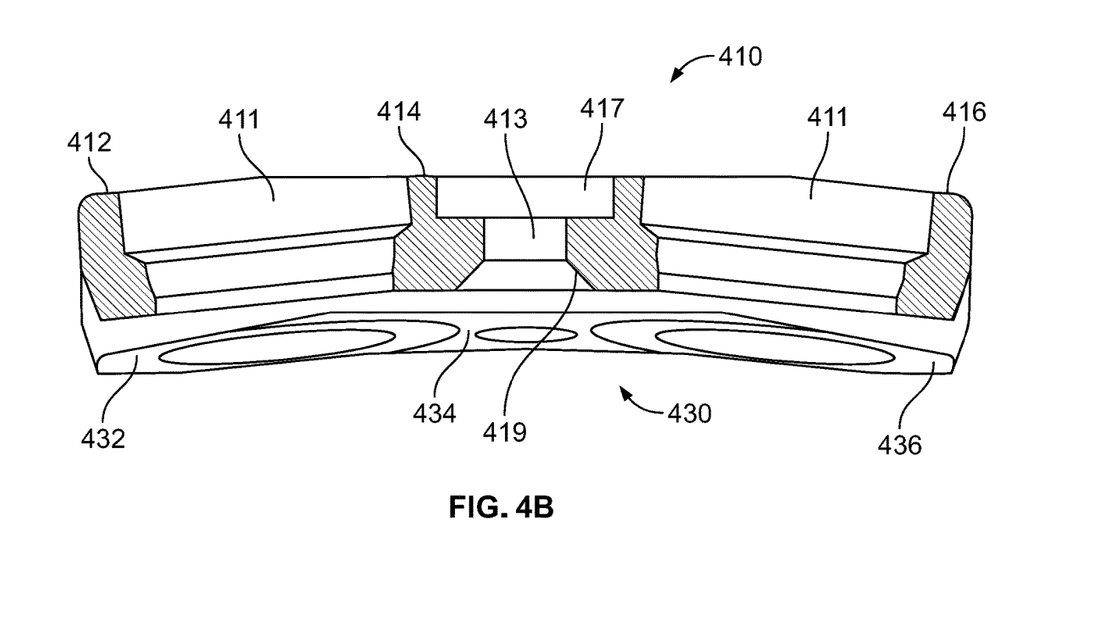
FIG. 4B is a cross-sectional view of the bone plate of FIG. 4A taken along line B-B.
Figure 4C:
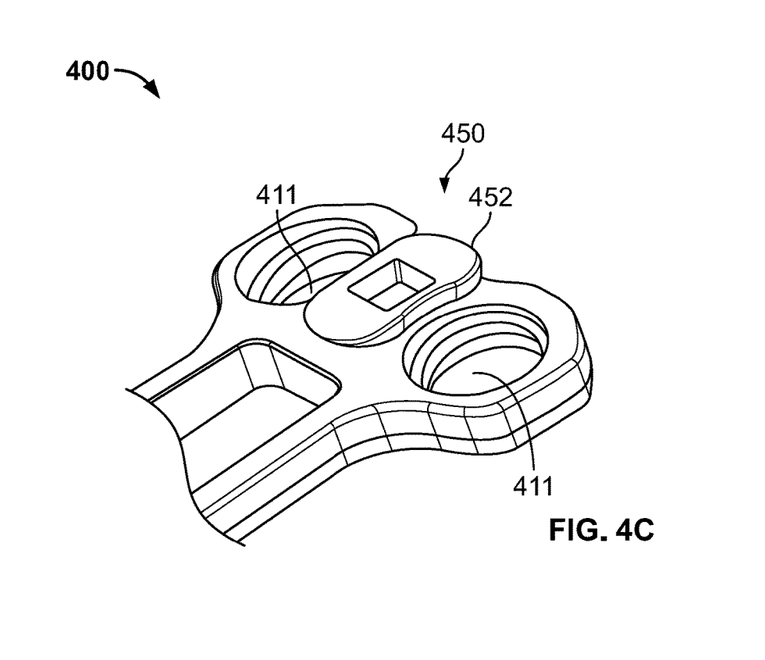
FIG. 4C is a partial perspective view of the bone plate of FIG. 4A in conjunction with another screw blocker embodiment shown in a first configuration.
Figure 4D:
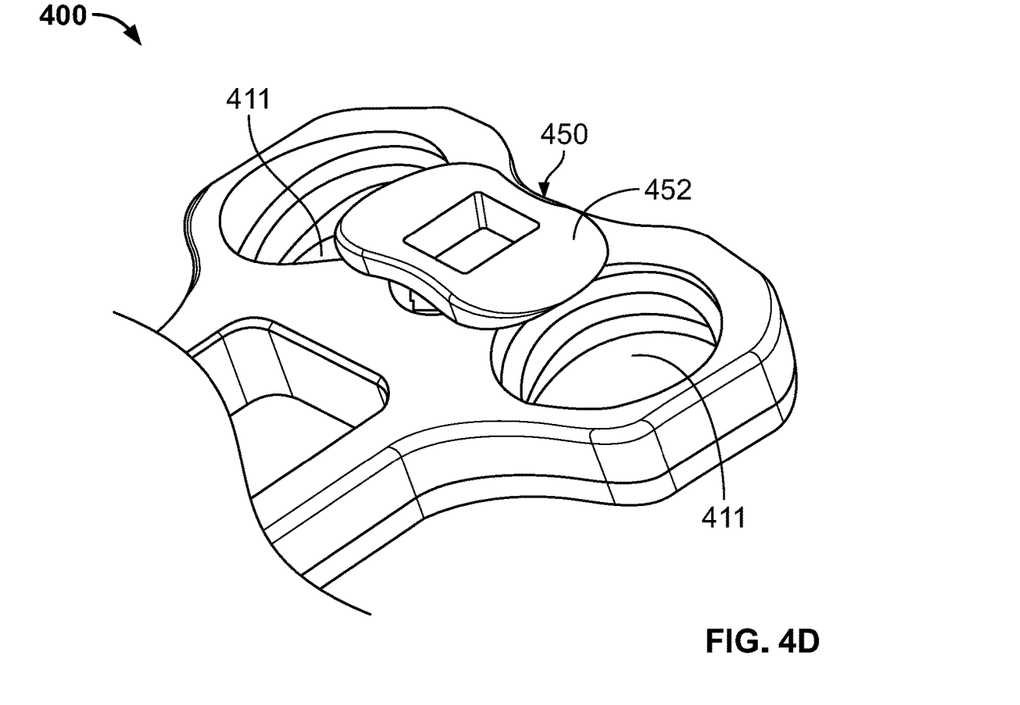
FIG. 4D is a partial perspective view of the bone plate of FIG. 4A with the bone screw blocker in a second configuration.

FIGS. 4A-4E depict an even further embodiment bone plate 400. For ease of review, like elements are accorded like reference numerals to that of bone plate 100, but within the 400-series of numbers. For instance, bone plate 400 includes an upper surface 410 defined by flats 412, 414 and 416, and a bone contacting surface 430 defined by flats 432, 434 and 436, as best shown in FIG. 4B. However, bone plate 400 is configured to receive an alternative screw blocker 450. In this regard, plate 400 includes ovular shaped recesses 417 adjacent upper surface 410 that are each concentric with a smooth bore 413. Such smooth bores 413 flare outwardly into a conical shaped portion 419 adjacent bone contacting surface 430, as best shown in FIG. 4B. Ovular shaped recesses 417 also includes projections 418 that extend from a sidewall of plate 400 that are formed by recesses 417.

Figure 4E:
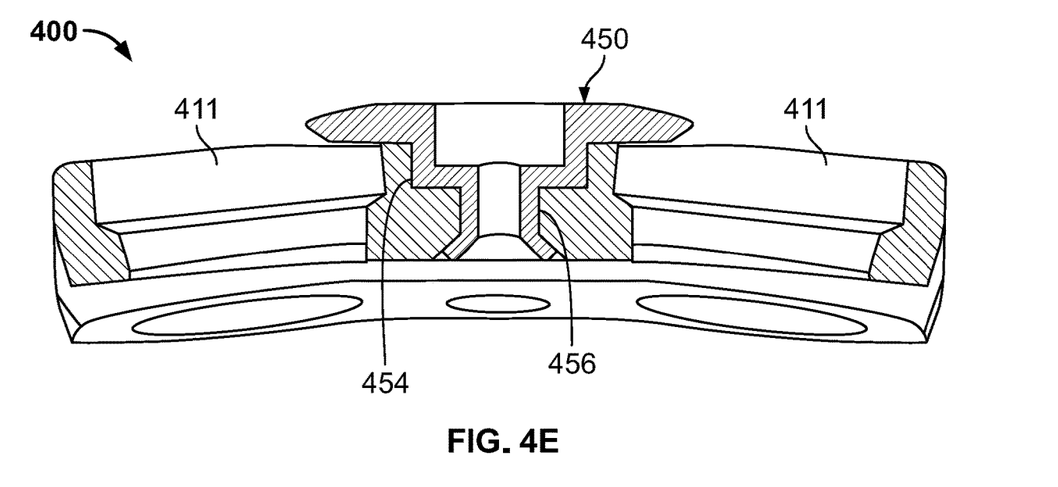
FIG. 4E is a cross-sectional view of the bone plate of FIG. 4A and the screw blocker while in the second configuration.

Blocker 450 includes an elongate head 450, a boss 454 extending from head 450, and a shaft 456 extending from boss 454. As shown in FIG. 4E, boss 454 is received in ovular recess 417, and shaft 456 is received in smooth bore 413. Blocker 450 is riveted so as to be secured to plate 400. In this regard, a free end of shaft 456 is deformed so as to conform to the flared end 419 of smooth bore 413 thereby prohibiting removal of blocker 450 from bore 413. This allows blocker 450 to freely rotate from a first configuration (see FIG. 4C) in which blocker head 452 is oriented to allow bone screws to be received in openings 411, and a second configuration (see FIGS. 4D and 4E) in which blocker head 452 is oriented so as to extend partially over openings 411 and any bone screws positioned therein. Projections 418 engage corresponding recesses (not shown) in boss 454 when blocker 450 is in the second configuration which maintains blocker 450 in this configuration until a deliberate action rotates blocker 450 back to the first configuration.

Bone plates 200, 300, and 400 can vary in many ways, including in accordance with the above-discussed variations of plate 100. For instance, although shown as being a two-level bone plate, bone plates similar to bone plates 200, 300, and 400 can be made for use in the fusion of any number of levels of the spine.

In use, bone plates 100, 200, 300 and 400 are utilized largely in the same manner as existing bone plates. A suitably sized plate is chosen and placed against the vertebral bodies to be fused. Prior to the insertion of screws through holes 111, 211, 311, 411, a drill and drill guide may be utilized to drill screw holes into those vertebrae. It is also contemplated to utilize a trial implant during the initial drilling of the screw holes. The disc space between the vertebrae may be packed with bone graft material, either before placement of the plate or after with the aid of graft windows 115, 215, 315, 415. Thereafter, screws may be placed through the individual screw holes and into the drilled holes of the vertebrae. Blockers may be placed into blocker holes 113, 213, 313, 413 after the placement of screws, or already included blockers may be actuated from a position that allowed the screws to be placed to a blocking position.

At some point during the above-described general surgical method, bone plates 100, 200, 300 or 400 may need to be bent or otherwise manipulated into a form suitable for placement in a given patient. The inclusion of the above-described flat surfaces makes this bending process easier, as well as improves the seating of the plates against the vertebrae, as discussed above. This ultimately makes the placement of screws through holes 111, 211, 311, 411 easier, and prevents much of the inadvertent "rocking" associated with traditional bone plates.

While bone plates 100, 200, 300, and 400 are shown as anterior cervical plates, it is to be understood that the present invention has applicability to any type of bone plate. Indeed, it is contemplated to incorporate certain of the inventive features of the present invention in bone plates designed for other uses. By way of example, plates designed for fracture fixation may benefit from the inclusion of flats or channel countersinks, as described above. Those types of plates may include, in addition to the locking and non-locking holes described above, compression holes or the like. In addition, plates according the present invention may be designed for use in other areas of the spine or to be applied in different orientations in the spine. For instance, lateral lumbar fusion plates are contemplated and may include similar structure to plates 100, 200, 300, and 400. It is to be understood that plates 100, 200, 300, and 400 are merely example plates and differently sized and shaped bone plates may include any of the various features described herein.

Finally, it is contemplated to form the bone plates of any type of material suitable for implantation within the body, or even multiple materials. With regards to the latter, it is contemplated to utilize softer material within the bone screw holes of the plates so as to facilitate deformation when a bone screw is placed therethrough. Examples of such screw holes are disclosed in U.S. Pat. No. 6,322,562, the disclosure of which is hereby incorporated by reference herein. The plates according to the present invention may be provided in a kit along with screws, blockers and other instrumentation necessary for their implantation. Again, blockers for use with the plates may be incorporated into the plate (i.e., not removable) or could be designed to be placed in the plates by a surgeon. Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone plate comprising:
an upper surface defined by at least two flat surfaces; and
a bone contacting surface defined by three flat surfaces intersecting each other at a first angle,
wherein the three flat surfaces that comprise the bone contacting surfaces intersect each other at respective interfaces that extends in a longitudinal direction of the bone plate such that a first flat surface and a third flat surface of the three flat surfaces depend downwardly from opposite sides of a second flat surface of the three flat surfaces.

2. The bone plate of claim 1, further comprising two bone screw holes and two blocker holes.

3. The bone plate of claim 2, further comprising a countersink extending between and at least partially surrounding the two blocker holes.

4. The bone plate of claim 3, wherein the countersink is defined by a channel extending along a length of the plate, the length of the channel being greater than a width thereof.

5. The bone plate of claim 4, further comprising two bone screw holes, a blocker hole disposed between the two bone screw holes and within the channel, and a blocker disposed in the blocker hole.

6. The bone plate of claim 1, wherein the bone plate is an anterior cervical plate having first and second bone screw holes configured for introducing first and second bone screws into two vertebrae, respectively.

7. A bone plate comprising:
an upper surface;
a bone contacting surface;
at least two bone screw holes; and
first and second blocker holes at least partially surrounded by a channel depressed in the upper surface and extending from the first blocker hole to the second blocker hole,
wherein the channel has a length extending along length of the plate and a width extending transverse to the length of the plate, the length of the channel being greater than the width,
wherein the lower surface includes at least three flat surfaces such that a first and second flat surface intersect each other at a first interface extending in a longitudinal direction and the second flat surface and a third flat surface intersect each other at a second interface extending in the longitudinal direction, the first and third flat surfaces depending downwardly from the second flat surface.

8. The bone plate of claim 7, wherein the upper surface includes at least three flat surfaces such that a first and second flat surface of the upper surface intersect each other at a first interface of the upper surface extending in a longitudinal direction, and the first flat surface of the upper surface and a third flat surface of the upper surface intersect at an interface that extends in the transverse direction.

9. The bone plate of claim 8, wherein the upper surface includes five flat surfaces and the bone contacting surface includes five flat surfaces.

10. The bone plate of claim 7, further comprising two bone screw holes, a blocker hole disposed between the two bone screw holes and a blocker disposed in the blocker hole.

11. The bone plate of claim 10, wherein the blocker is movable between a first position in which bone screws can be placed in the bone screw holes and a second position in which the bone screws are prevented from removal from the bone screw holes.

12. The bone plate of claim 1, wherein the at least two flat surfaces that comprise the upper surface are each planar in two orthogonal planes.

13. The bone plate of claim 12, wherein the two orthogonal planes include a cranial-caudal plane and a medial-lateral plane.

14. The bone plate of claim 1, wherein the at least two flat surfaces of the upper surface include three flat surfaces and only three flat surfaces.

15. The bone plate of claim 7, wherein the channel extends along the entire length of the plate.

16. The bone plate of claim 7, wherein a window is situated between the first and second blocker holes and intersects the channel.

17. The bone plate of claim 7, wherein the channel includes first and second flat surfaces, the first and second flat surfaces intersecting each other at an angle.

18. The bone plate of claim 7, wherein the channel includes a plurality of blocker holes each positioned adjacent to a pair of screw holes.

19. The bone plate of claim 7, wherein the lower surface includes a fourth flat surface intersecting the third flat surface at an interface that extends in a transverse direction perpendicular to the longitudinal direction.

* * * * *